(12) United States Patent
Morishima et al.

(10) Patent No.: US 6,280,942 B1
(45) Date of Patent: Aug. 28, 2001

(54) ENDONUCLEASE

(75) Inventors: Nobuhiro Morishima; Hikaru Mizumura; Takehiko Shibata, all of Saitama (JP)

(73) Assignee: Institute of Physical and Chemical Research, Saitama (JP)

( * ) Notice: Subject to any disclaimer, the term of this patent is extended or adjusted under 35 U.S.C. 154(b) by 0 days.

(21) Appl. No.: 09/316,083

(22) Filed: May 20, 1999

(30) Foreign Application Priority Data

May 22, 1998 (JP) .................................................. 10-141861

(51) Int. Cl.⁷ .............................. C12Q 1/68; C12P 19/34
(52) U.S. Cl. .............................. 435/6; 435/91.1; 435/190
(58) Field of Search ............................... 435/190, 6, 91.1

(56) References Cited

FOREIGN PATENT DOCUMENTS 4-104793   4/1992  (JP) .

OTHER PUBLICATIONS

Nakagawa, K., et al. (1991) J. Biol. Chem. 266(3), 1977–1984.*

Seraphin, B., et al. (1987) J. Biol. Chem. 262(21), 10146–10153.*

Colleaux, L., et al.(1986) Cell 44, 521–533.*

Sutherland et al., "Multisite oligonucleotide–mediated mutagenesis: Application to the conversion of a mitochondrial gene to universal genetic code," Biotechniques, Eaton Publishing, Natick, US, vol. 18, No. 3 (1995) pp. 458, 460, 463–464.

Mizamura et al., "Stable association of 70–kDa heat shock protein induces latent multisite specificity of a unisite–specific endonuclease in yeast mitochondria," The Journal of Biological Chemistry, vol. 274, No. 36 (1999) pp. 25682–25690.

* cited by examiner

Primary Examiner—Charles L. Patterson, Jr.
(74) Attorney, Agent, or Firm—Fish & Richardson P.C.

(57) ABSTRACT

The present invention relates to a site-specific endonuclease which recognizes a specific nucleotide sequence, to a gene coding for the endonuclease, to a recombinant vector containing the gene, to a transformant containing the vector, and to a process for producing the endonuclease.

2 Claims, 7 Drawing Sheets

FIG. 1

```
                                              33 35     40      45 4849
         MKKQNLNSIL LMYINYIINY FNNIHKNQLK KD.IIEYEYT YKFLINNILC
         MKKQNLNSIL LMYINYIINY FNNIHKNQLK KDWIMEYEYM YKFLMNNMTC   50
   54         65          80         86        92     99         107109
FIK.DNNKIL LLLDIYYNVL YNYHKORTPI SNKRLINSKN IIDYKLLYLY FYILNKIKIE
FIKWDNNKIL LLLDMYYNVL YNYHKQRTPM SNKRLMNSKN IMDYKLLYTY FYILNKMKME  110
111            123        130        135        154       163 168
IDNYNNNNNN ISLKYNELLK NIINNLNYKL SNIELNLSNN FYLIDKYLIN KYIKYLDILN
MDNYNNNNNN ISLKYNELLK NIMNNLNYKT SNIETNLSNN FYLMDKYLIN KYMKYLDMLN  170
171  177                                         217     222
IIPNNYIFNN INYKGKLNIK TVLDLNNNEF YDYLSGLIEG DGYIGPGGIT ILNHANDVLN
MIPNNYMFNN INYKGKLNIK TVLDLNNNEF YDYLSGLIEG DGYIGPGGIT ITNHANDVLN  230
              247248                   267        276
TIFINKRIKN SILVEK.IDT LKDNPYFVNA FSINIKLNLA KEKIFLNIYN KLYSDYKINQ
TIFINKRIKN SILVEKWMDT LKDNPYFVNA FSINIKTNLA KEKIFTNIYN KLYSDYKINQ  290
                     313     320                    335     346347
INNHIPYYNY LKINNKLPIK NIIDIKNNY. LAGFTAADGS FLSSIYNPKD TLLFKNIRPS
INNHIPYYNY LKINNKLPIK NIMDIKNNYW LAGFTAADGS FLSSMYNPKD TLLFKNMRPS  350
                                               395 399
YVISOVETRK ELIYLIQESF DLSISNVKKV GNRKLKDFKL FTRTLDELIK FIYYFDKFLP
YVISQVETRK ELIYLIQESF DLSISNVKKV GNRKLKDFKL FTRTTDELMK FIYYFDKFLP  410
              426     433                                    465
LHDNKQFNYI KFRFNLFIKS YN.NNRVFGL VLSEYINNIK IDNYDYYYYN KYINIHNARK
LHDNKQFNYI KFRFNTFIKS YNWNNRVFGL VLSEYINNIK IDNYDYYYYN KYINMHNARK  470

PKGYIK.
PKGYIK.  476
```

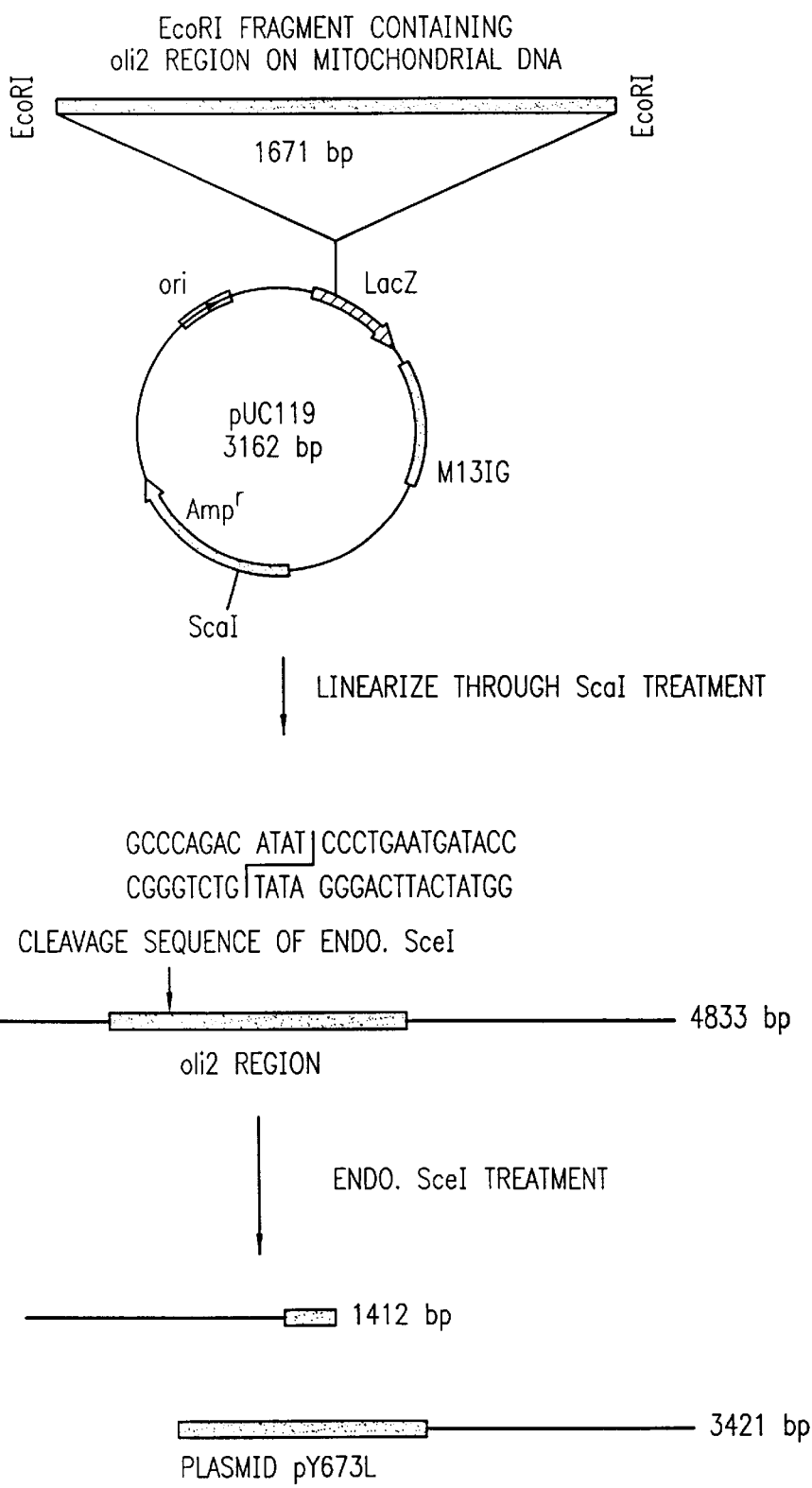

PLASMIDS pEN1.7 AND pEN0.5

FIG. 4

```
ATGAAAAAACAAAATTTAAATTCTATTTTATTAATGTATATTAATTATATTATTAATTATTTTAATAATA        70

TTCATAAAAATCAATTAAAAAAAGACTGGATTATGGAATATGAATATATGTATAAATTTTTAATGAATAA        140
              A     A                A                 A
TATGACTTGTTTTATTAAATGGGATAATAATAAAATTTTATTATTATTAGATATATGTTATAATGTATTA        210
    ACTA     A                                              A
TATAACTATCATAAACAACGTACACCTATGTCTAATAAAAGATTAATGAATTCAAAAAATATTATGGATT        280
                    A                A                     A
ATAAATTATTATATACTTATTTTTATATTTTAAATAAAATGAAAATGGAAATGGATAATTATAATAATAA        350
            CT                    A     A    A
TAATAATAATATTTCATTAAAATATAATGAATTATTAAAAAATATTATGAATAATTTAAATTATAAAACT        420
                                     A                            CTA
TCTAATATTGAAACTAATTTATCTAATAATTTTTATTTAATGGATAAATATTTAATTAATAAATATATGA        490
       CT                       A                    A
AATATTTAGATATGTTAAATATGATTCCTAATAATTATATGTTTAATAATATTAATTATAAAGGTAAATT        560
    A          A                      A
AAATATTAAAACAGTATTAGATTTAAATAATAATGAATTTTATGATTATTTATCAGGGTTAATTGAAGGT        630

GATGGTTATATTGGTCCTGGAGGTATTACAATTACTAATCATGCTAATGATGTATTAAATACTATCTTTA        700
                                CTA
TTAATAAAAGAATTAAAAATAGTATTTTAGTAGAAAAATGGATGGATACTTTAAAAGATAATCCTTATTT        770
                                             A  A
TGTTAATGCTTTCTCTATTAATATTAAAACTAATTTAGCTAAAGAAAAGATTTTTACTAATATTTATAAT        840
                 CT                                  CT
AAATTATATAGTGATTATAAAATTAATCAAATTAATAATCATATCCCTTATTATAATTATTTAAAAATTA        910

ATAATAAATTACCTATTAAAAATATTATGGATATTAAAAATAATTATTGGTTAGCTGGTTTTACAGCTGC        980
                A                   A
AGATGGTTCTTTTTTATCATCTATGTATAATCCTAAAGATACATTATTATTTAAAAATATGAGACCTAGT        1050
           A                                            A
TATGTTATTTCACAAGTTGAAACACGTAAAGAATTAATTTATTTAATTCAAGAATCTTTTGATTTATCTA        1120

TTTCTAATGTTAAAAAAGTTGGTAATAGAAAATTAAAAGATTTTAAATTATTTACCAGAACTACTGATGA        1190
                                                           CT
ATTAATGAAATTTATTTATTATTTTGATAAATTTTTACCTTTACATGATAATAAACAATTTAATTATATT        1260
 A
AAATTTAGATTTAATACTTTTATTAAATCATATAATTGGAATAATAGAGTATTTGGTTTAGTATTATCTG        1330
           CTA                     A
AATATATCAATAATATTAAAATTGATAATTATGATTATTATTATTATAATAAATATATTAATATGCATAA        1400
                                                          A
TGCACGTAAACCTAAAGGATACATTAAATAA    1431
```

SEQUENCE-SPECIFIC ENDONUCLEASE
ACTIVITY OF ENDOSceI 50 kDa SUBUNIT

SUBSTRATE pY673L 1  2  3  4  5  6  7  8

M: λ DNA HIND III MARKER
S: SUBSTRATE DNA ONLY

SUBSTRATE pBR322

1  2  3  4  5  6  7

M: λ DNA HIND III MARKER
S: SUBSTRATE DNA ONLY

50 KDA SUBUNIT (476 AMINO ACID RESIDUES)

|  | 217 | 346 |
|---|---|---|
| S. CEREVISIAE ENDO.SceI | Gly | Asn |
| S. UVARUM ENDO.SuvI | Lys | Asp |

35  GTTATATTGGTCCTAAAGGTATTACAATTA
          (GG)

36  ATTATTTAAAGATATGAGA
          (A)

FIG. 7A
SEQUENCE-SPECIFIC ENDONUCLEASE
ACTIVITY OF ENDO.SuvI 50 kDa SUBUNIT
ENDO.SuvI 50 KDA SUBUNIT
SUBSTRATE pY673L
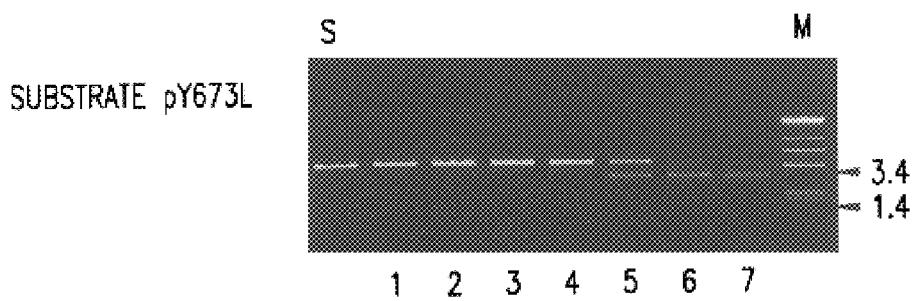
— 3.4
— 1.4
1 2 3 4 5 6 7
ENDO.SceI 50 kDa SUBUNIT
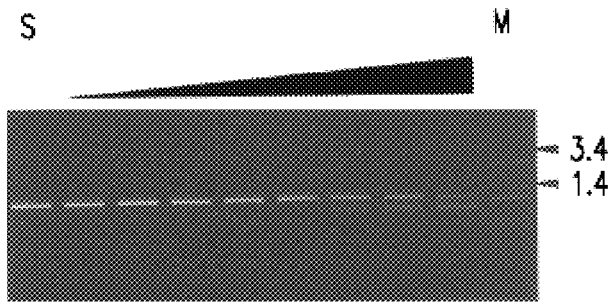
— 3.4
— 1.4
M: λ DNA HIND III MARKER
S: SUBSTRATE DNA ONLY
FIG. 7B
ENDO.SuvI 50 KDA SUBUNIT
SUBSTRATE pBR322
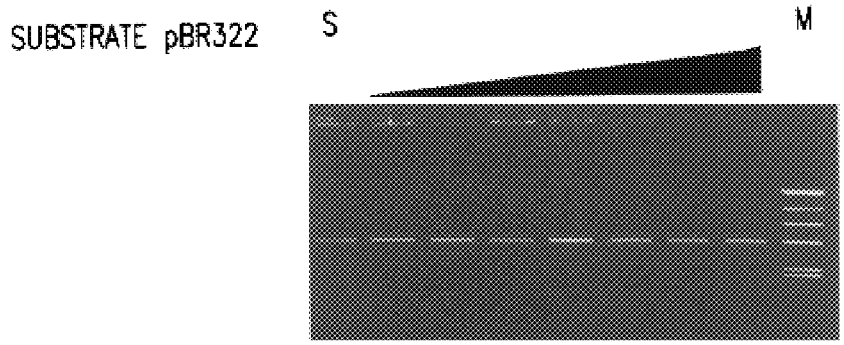
M: λ DNA HIND III MARKER
S: SUBSTRATE DNA ONLY

SEQUENCE LISTING

```
<160> NUMBER OF SEQ ID NOS: 38

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 1
gcccagacat atccctgaat gatacc                                          26

<210> SEQ ID NO 2
<211> LENGTH: 1431
<212> TYPE: DNA
<213> ORGANISM: Saccharomyces cerevisiae
<220> FEATURE:
<221> NAME/KEY: CDS
<222> LOCATION: (1)..(1428)

<400> SEQUENCE: 2 atg aaa aaa caa aat tta aat tct att tta tta atg tat att aat tat      48
Met Lys Lys Gln Asn Leu Asn Ser Ile Leu Leu Met Tyr Ile Asn Tyr
  1               5                  10                  15 att att aat tat ttt aat aat att cat aaa aat caa tta aaa aaa gac      96
```

```
Ile Ile Asn Tyr Phe Asn Asn Ile His Lys Asn Gln Leu Lys Lys Asp
            20                  25                  30 tgg att atg gaa tat gaa tat atg tat aaa ttt tta atg aat aat atg      144
Trp Ile Met Glu Tyr Glu Tyr Met Tyr Lys Phe Leu Met Asn Asn Met
        35                  40                  45 act tgt ttt att aaa tgg gat aat aat aaa att tta tta tta gat          192
Thr Cys Phe Ile Lys Trp Asp Asn Asn Lys Ile Leu Leu Leu Asp
50                  55                  60 atg tat tat aat gta tta tat aac tat cat aaa caa cgt aca cct atg      240
Met Tyr Tyr Asn Val Leu Tyr Asn Tyr His Lys Gln Arg Thr Pro Met
65                  70                  75                  80 tct aat aaa aga tta atg aat tca aaa aat att atg gat tat aaa tta      288
Ser Asn Lys Arg Leu Met Asn Ser Lys Asn Ile Met Asp Tyr Lys Leu
            85                  90                  95 tta tat act tat ttt tat att tta aat aaa atg aaa atg gaa atg gat      336
Leu Tyr Thr Tyr Phe Tyr Ile Leu Asn Lys Met Lys Met Glu Met Asp
            100                 105                 110 aat tat aat aat aat aat aat aat att tca tta aaa tat aat gaa tta      384
Asn Tyr Asn Asn Asn Asn Asn Asn Ile Ser Leu Lys Tyr Asn Glu Leu
            115                 120                 125 tta aaa aat att atg aat aat tta aat tat aaa act tct aat att gaa      432
Leu Lys Asn Ile Met Asn Asn Leu Asn Tyr Lys Thr Ser Asn Ile Glu
130                 135                 140 act aat tta tct aat aat ttt tat tta atg gat aaa tat tta att aat      480
Thr Asn Leu Ser Asn Asn Phe Tyr Leu Met Asp Lys Tyr Leu Ile Asn
145                 150                 155                 160 aaa tat atg aaa tat tta gat atg tta aat atg att cct aat aat tat      528
Lys Tyr Met Lys Tyr Leu Asp Met Leu Asn Met Ile Pro Asn Asn Tyr
                165                 170                 175 atg ttt aat aat att aat tat aaa ggt aaa tta aat att aaa aca gta      576
Met Phe Asn Asn Ile Asn Tyr Lys Gly Lys Leu Asn Ile Lys Thr Val
            180                 185                 190 tta gat tta aat aat aat gaa ttt tat gat tat tta tca ggg tta att      624
Leu Asp Leu Asn Asn Asn Glu Phe Tyr Asp Tyr Leu Ser Gly Leu Ile
            195                 200                 205 gaa ggt gat ggt tat att ggt cct gga ggt att aca att act aat cat      672
Glu Gly Asp Gly Tyr Ile Gly Pro Gly Gly Ile Thr Ile Thr Asn His
210                 215                 220 gct aat gat gta tta aat act atc ttt att aat aaa aga att aaa aat      720
Ala Asn Asp Val Leu Asn Thr Ile Phe Ile Asn Lys Arg Ile Lys Asn
225                 230                 235                 240 agt att tta gta gaa aaa tgg atg gat act tta aaa gat aat cct tat      768
Ser Ile Leu Val Glu Lys Trp Met Asp Thr Leu Lys Asp Asn Pro Tyr
                245                 250                 255 ttt gtt aat gct ttc tct att aat att aaa act aat tta gct aaa gaa      816
Phe Val Asn Ala Phe Ser Ile Asn Ile Lys Thr Asn Leu Ala Lys Glu
            260                 265                 270 aag att ttt act aat att tat aat aaa tta tat agt gat tat aaa att      864
Lys Ile Phe Thr Asn Ile Tyr Asn Lys Leu Tyr Ser Asp Tyr Lys Ile
            275                 280                 285 aat caa att aat aat cat atc cct tat tat aat tat tta aaa att aat      912
Asn Gln Ile Asn Asn His Ile Pro Tyr Tyr Asn Tyr Leu Lys Ile Asn
            290                 295                 300 aat aaa tta cct att aaa aat att atg gat att aaa aat aat tat tgg      960
Asn Lys Leu Pro Ile Lys Asn Ile Met Asp Ile Lys Asn Asn Tyr Trp
305                 310                 315                 320 tta gct ggt ttt aca gct gca gat ggt tct ttt tta tca tct atg tat     1008
Leu Ala Gly Phe Thr Ala Ala Asp Gly Ser Phe Leu Ser Ser Met Tyr
                325                 330                 335
```

```
aat cct aaa gat aca tta tta ttt aaa aat atg aga cct agt tat gtt      1056
Asn Pro Lys Asp Thr Leu Leu Phe Lys Asn Met Arg Pro Ser Tyr Val
        340                 345                 350 att tca caa gtt gaa aca cgt aaa gaa tta att tat tta att caa gaa      1104
Ile Ser Gln Val Glu Thr Arg Lys Glu Leu Ile Tyr Leu Ile Gln Glu
            355                 360                 365 tct ttt gat tta tct att tct aat gtt aaa aaa gtt ggt aat aga aaa      1152
Ser Phe Asp Leu Ser Ile Ser Asn Val Lys Lys Val Gly Asn Arg Lys
    370                 375                 380 tta aaa gat ttt aaa tta ttt acc aga act act gat gaa tta atg aaa      1200
Leu Lys Asp Phe Lys Leu Phe Thr Arg Thr Thr Asp Glu Leu Met Lys
385                 390                 395                 400 ttt att tat tat ttt gat aaa ttt tta cct tta cat gat aat aaa caa      1248
Phe Ile Tyr Tyr Phe Asp Lys Phe Leu Pro Leu His Asp Asn Lys Gln
                405                 410                 415 ttt aat tat att aaa ttt aga ttt aat act ttt att aaa tca tat aat      1296
Phe Asn Tyr Ile Lys Phe Arg Phe Asn Thr Phe Ile Lys Ser Tyr Asn
            420                 425                 430 tgg aat aat aga gta ttt ggt tta gta tta tct gaa tat atc aat aat      1344
Trp Asn Asn Arg Val Phe Gly Leu Val Leu Ser Glu Tyr Ile Asn Asn
    435                 440                 445 att aaa att gat aat tat gat tat tat tat tat aat aaa tat att aat      1392
Ile Lys Ile Asp Asn Tyr Asp Tyr Tyr Tyr Tyr Asn Lys Tyr Ile Asn
450                 455                 460 atg cat aat gca cgt aaa cct aaa gga tac att aaa taa                  1431
Met His Asn Ala Arg Lys Pro Lys Gly Tyr Ile Lys
465                 470                 475
```

<210> SEQ ID NO 3
<211> LENGTH: 476
<212> TYPE: PRT
<213> ORGANISM: Saccharomyces cerevisiae

<400> SEQUENCE: 3

```
Met Lys Lys Gln Asn Leu Asn Ser Ile Leu Leu Met Tyr Ile Asn Tyr
  1               5                  10                  15

Ile Ile Asn Tyr Phe Asn Asn Ile His Lys Asn Gln Leu Lys Lys Asp
             20                  25                  30

Trp Ile Met Glu Tyr Glu Tyr Met Tyr Lys Phe Leu Met Asn Asn Met
         35                  40                  45

Thr Cys Phe Ile Lys Trp Asp Asn Asn Lys Ile Leu Leu Leu Leu Asp
     50                  55                  60

Met Tyr Tyr Asn Val Leu Tyr Asn Tyr His Lys Gln Arg Thr Pro Met
 65                  70                  75                  80

Ser Asn Lys Arg Leu Met Asn Ser Lys Asn Ile Met Asp Tyr Lys Leu
                 85                  90                  95

Leu Tyr Thr Tyr Phe Tyr Ile Leu Asn Lys Met Lys Met Glu Met Asp
            100                 105                 110

Asn Tyr Asn Asn Asn Asn Asn Ile Ser Leu Lys Tyr Asn Glu Leu
        115                 120                 125

Leu Lys Asn Ile Met Asn Leu Asn Tyr Lys Thr Ser Asn Ile Glu
    130                 135                 140

Thr Asn Leu Ser Asn Asn Phe Tyr Leu Met Asp Lys Tyr Leu Ile Asn
145                 150                 155                 160

Lys Tyr Met Lys Tyr Leu Asp Met Leu Asn Met Ile Pro Asn Asn Tyr
                165                 170                 175

Met Phe Asn Asn Ile Asn Tyr Lys Gly Lys Leu Asn Ile Lys Thr Val
            180                 185                 190
```

Leu Asp Leu Asn Asn Glu Phe Tyr Asp Tyr Leu Ser Gly Leu Ile
        195                 200                 205

Glu Gly Asp Gly Tyr Ile Gly Pro Gly Ile Thr Ile Thr Asn His
        210                 215                 220

Ala Asn Asp Val Leu Asn Thr Ile Phe Ile Asn Lys Arg Ile Lys Asn
225                 230                 235                 240

Ser Ile Leu Val Glu Lys Trp Met Asp Thr Leu Lys Asp Asn Pro Tyr
                245                 250                 255

Phe Val Asn Ala Phe Ser Ile Asn Ile Lys Thr Asn Leu Ala Lys Glu
                260                 265                 270

Lys Ile Phe Thr Asn Ile Tyr Asn Lys Leu Tyr Ser Asp Tyr Lys Ile
                275                 280                 285

Asn Gln Ile Asn Asn His Ile Pro Tyr Tyr Asn Tyr Leu Lys Ile Asn
                290                 295                 300

Asn Lys Leu Pro Ile Lys Asn Ile Met Asp Ile Lys Asn Asn Tyr Trp
305                 310                 315                 320

Leu Ala Gly Phe Thr Ala Ala Asp Gly Ser Phe Leu Ser Ser Met Tyr
                325                 330                 335

Asn Pro Lys Asp Thr Leu Leu Phe Lys Asn Met Arg Pro Ser Tyr Val
                340                 345                 350

Ile Ser Gln Val Glu Thr Arg Lys Glu Leu Ile Tyr Leu Ile Gln Glu
                355                 360                 365

Ser Phe Asp Leu Ser Ile Ser Asn Val Lys Lys Val Gly Asn Arg Lys
                370                 375                 380

Leu Lys Asp Phe Lys Leu Phe Thr Arg Thr Thr Asp Glu Leu Met Lys
385                 390                 395                 400

Phe Ile Tyr Tyr Phe Asp Lys Phe Leu Pro Leu His Asp Asn Lys Gln
                405                 410                 415

Phe Asn Tyr Ile Lys Phe Arg Phe Asn Thr Phe Ile Lys Ser Tyr Asn
                420                 425                 430

Trp Asn Asn Arg Val Phe Gly Leu Val Leu Ser Glu Tyr Ile Asn Asn
                435                 440                 445

Ile Lys Ile Asp Asn Tyr Asp Tyr Tyr Tyr Asn Lys Tyr Ile Asn
450                 455                 460

Met His Asn Ala Arg Lys Pro Lys Gly Tyr Ile Lys
465                 470                 475

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 4
ccggatccat gaaaaaac                                                     18

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 5

-continued

```
gggtcgactt atttaatgta tcc                                           23
```

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 6

```
aaaagactgg attatagaa                                                19
```

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 7

```
tgaatatatg tataaattt                                                19
```

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 8

```
tattaaatgg gataataat                                                19
```

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 9

```
tattagatat gtattataat g                                             21
```

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 10

```
tacacctatg tctaataaa                                                19
```

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 11

```
aaaatattat ggattataaa                                               20
```

<210> SEQ ID NO 12
<211> LENGTH: 52
<212> TYPE: DNA
<213> ORGANISM: Artificial Sequence
<220> FEATURE:
<223> OTHER INFORMATION: Description of Artificial Sequence:Synthetic DNA

<400> SEQUENCE: 12
ttttatattt taaataaaat gaaaatggaa atggataatt ataataataa ta    52

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence:Synthetic DNA

<400> SEQUENCE: 13
aaaatattat gaataattta a    21

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence:Synthetic DNA

<400> SEQUENCE: 14
actatctaat attgaaacta atttatctaa taattt    36

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence:Synthetic DNA

<400> SEQUENCE: 15
ttatttaatg gataaatat    19

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence:Synthetic DNA

<400> SEQUENCE: 16
ataaatatat gaaatattta g    21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence:Synthetic DNA

<400> SEQUENCE: 17
ataattatat gtttaataat a    21

```
<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 18
ggaggtatta caattactaa tcatgctaat gat                          33

<210> SEQ ID NO 19
<211> LENGTH: 36
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 19
ttttagtaga aaaatggatg gatactttaa aagata                       36

<210> SEQ ID NO 20
<211> LENGTH: 39
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 20
agctaaagaa aagattttta ctaatattta taataatta                    39

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 21
aaatattatg gatattaaa                                          19

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 22
taattattgg ttatctgg                                           18

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 23
atcatctatg tataatcct                                          19
```

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 24
ttaaaaatat gagacctag                                                  19

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 25
gatgaattaa tgaaatttat tta                                             23

<210> SEQ ID NO 26
<211> LENGTH: 39
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 26
attaaattta gatttaatac ttttattaaa tcatataat                            39

<210> SEQ ID NO 27
<211> LENGTH: 38
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 27
tataataaat atattaatat gcataatgca cgtaaacc                             38

<210> SEQ ID NO 28
<211> LENGTH: 42
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 28
taaattttta ataaataata tgacttgttt tattaaatgg ga                        42

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 29
aagattaatg aattcaaaa                                                  19

<210> SEQ ID NO 30

```
<211> LENGTH: 39
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 30
gattataaat tattatatac ttattttat attttaaat                              39

<210> SEQ ID NO 31
<211> LENGTH: 38
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 31
gaataattta aattataaaa cttctaatat tgaaacta                              38

<210> SEQ ID NO 32
<211> LENGTH: 37
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 32
ttctctatta atattaaaac taatttagct aaagaaa                               37

<210> SEQ ID NO 33
<211> LENGTH: 38
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 33
aaattattta ccagaactac tgatgaatta atgaaatt                              38

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 34
catataattg gaataataga                                                  20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 35 aattttaat gaataatatg                                                   20

<210> SEQ ID NO 36
<211> LENGTH: 19
```

```
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 36
tttagatatg ttaaatatg                                              19

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 37
atatgttaaa tatgattcct aataa                                       25

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 38
ctggattatg gaatatgaat                                             20
```

ENDONUCLEASE

FIELD OF THE INVENTION

The present invention relates to a site-specific endonuclease which recognizes a specific nucleotide sequence, to a gene coding for the endonuclease, to a recombinant vector containing the gene, to a transformant containing the vector, and to a process for producing the endonuclease.

BACKGROUND OF THE INVENTION

Endonuclease is a nuclease (nucleic acid degrading enzyme) which hydrolyzes the phosphodiester bond of a polynucleotide chain. Endonuclease recognizes and binds to a specific nucleotide sequence along DNA molecules, whereby molecules within the recognition sequence is cut. Endonuclease is a requisite enzyme for today's advanced gene engineering techniques for cloning and analyzing genes.

A site-specific endonuclease Endo.SceI (hereinafter, also referred to as "SceI") from an eucaryotic microorganism (e.g., yeast) is known to be a heterodimer having subunits of 75 kDa and 50 kDa. The subunits of SceI as well as genes encoding the subunits have been cloned, and the nucleotide sequences thereof have been determined (for 75 kDa subunit, see Morishima, N. et al., J. Biol. Chem. 265, 15189–15197 (1990) and for 50 kDa subunit, see JP-B-7-77556).

In order to widely utilize the above-described endonuclease for artificially modifying a biochemical agent, a gene or the like, the endonuclease needs to be mass-produced with a gene expression system. The endonuclease does not function unless it recognizes a specific nucleotide sequence, i.e., the endonuclease needs to be specific to the nucleotide sequence to be recognized.

The 50 kDa subunit of the above-described endonuclease SceI is encoded by mitochondrial genomes of yeast (*Saccharomyces cerevisiae*). A gene of a mitochondrial genome of yeast contains codons unique to mitochondria which are different from amino acid codons (universal codons) used in gene expression systems from organisms generally used for mass expression of protein (*E.coli*, baculovirus, yeast, etc.). If this gene of the mitochondrial genome is directly used, the protein expression system hardly produces a protein of an original amino acid sequence. For example, while TGA is a stop codon as a universal codon, it is a different codon coding for other amino acid (Trp) in mitochondria. A gene may be normally expressed in mitochondria but expression of the same gene may not result in a complete protein in a general expression system such as *E.coli* due to incomplete translation caused by the stop codon.

SUMMARY OF THE INVENTION

The present invention aims at providing a site-specific endonuclease which recognizes a specific nucleotide sequence, to a gene coding for the endonuclease, to a recombinant vector containing the gene, to a transformant containing the vector, and to a process for producing the endonuclease.

The present inventors have gone through intensive studies to solve the above-described problems. As a result, they succeeded in producing a modified endonuclease capable of recognizing and cleaving a specific nucleotide sequence by substituting, in a gene encoding an amino acid sequence of the smaller subunit of an endonuclease from yeast, codons unique to mitochondria with universal codons, and in mass-expressing the endonuclease, whereby the present invention was accomplished.

Accordingly, the present invention relates to an endonuclease capable of recognizing the nucleotide sequence: GCCCAGACATATCCCTGAATGATACC.

Further, the present invention relates to a recombinant protein of either (a) or (b):
(a) a protein comprising the amino acid sequence represented by SEQ ID NO:3; or
(b) a protein having an endonuclease activity for recognizing the nucleotide sequence: GCCCAGACATATCCCTGAATGATACC, the protein comprising at least one deletion, substitution or addition of amino acid in the amino acid sequence represented by SEQ ID NO:3.

Moreover, the present invention relates to a gene encoding the recombinant protein of either (a) or (b):
(a) a protein comprising the amino acid sequence represented by SEQ ID NO:3; or
(b) a protein having an endonuclease activity for recognizing the nucleotide sequence: GCCCAGACATATCCCTGAATGATACC, the protein comprising at least one deletion, substitution or addition of amino acid in the amino acid sequence represented by SEQ ID NO:3.

In addition, the present invention relates to a gene containing DNA of either (c) or (d):
(c) DNA comprising the nucleotide sequence represented by SEQ ID NO:2; or
(d) DNA encoding a protein having an endonuclease activity for recognizing the nucleotide sequence: GCCCAGACATATCCCTGAATGATACC, the DNA being capable of hybridizing with DNA which comprises the nucleotide sequence represented by SEQ ID NO:2 under stringent conditions.

Furthermore, the present invention relates to a recombinant vector comprising the above-described gene.

Additionally, the present invention relates to a transformant comprising the above-described recombinant vector.

Moreover, the present invention relates to a process for producing the endonuclease, comprising the steps of:
culturing the above-described transformant; and
recovering from the culture an endonuclease capable of recognizing the nucleotide sequence: GCCCAGACATATCCCTGAATGATACC.

This specification includes part or all of the contents as disclosed in the specification and/or drawings of Japanese Patent Application No. 10-141861 which is a priority document of the present invention.

BRIEF DESCRIPTION OF THE DRAWINGS

FIG. 1 shows amino acid sequences of an endonuclease before and after the modification;

FIG. 2 shows the steps for constructing plasmid pY673L;

FIG. 4 shows the nucleotide sequence of 50 kDa subunit gene of SceI which has been modified to conform the universal code;

FIGS. 7A and 7B are photographs of electrophoresis showing sequence-specific endonuclease activities of the 50 kDa subunit from *Saccharomyces uvarum*.

DESCRIPTION OF THE PREFERRED EMBODIMENTS

Hereinafter, the present invention will be described in more detail.

The present invention aims at mass-expressing mitochondrial genome DNA encoding the smaller subunit (50 kDa) of an endonuclease from yeast by using a protein expression system such as *E.coli* or yeast. In accomplishing this aim, the present invention modifies, in a gene coding for an amino acid sequence of the smaller subunit, codons unique to mitochondria into universal codons. The present invention relates to such a modified smaller subunit capable of recognizing and cleaving 26 base pairs of the specific nucleotide sequence.

An endonuclease of the present invention (i.e., the 50 kDa subunit of an endonuclease from yeast; hereinafter also referred to as "Endo.ScelI 50 kDa") is prepared as follows.

(1) Designing mutated amino acid and introducing mutation

Figures 6A, 6B:
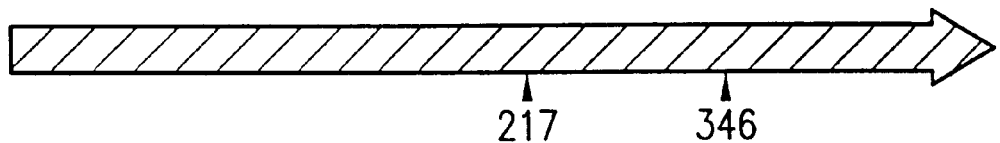
FIGS. 6A and 6B show substitution site of the 50 kDa subunit from *Saccharomyces uvarum* and oligonucleotides used for the substitution.

According to the present invention, the smaller subunit of endonuclease Scei from *Saccharomyces cerevisiae* or the smaller subunit of endonuclease SuvI from *Saccharomyces uvarum* is used as a target for introducing a mutation. The smaller subunits of both SceI and SuvI have molecular weights of 50 kDa. However, they differ from each other for having 2 different amino acids (FIG. 6A).

The gene coding for the subunit (50 kDa) of SceI (hereinafter, referred to as "ENS2") is encoded by a mitochondrial genome, and thus contains genetic codes unique to mitochondria (Table 1).

TABLE 1

Difference between mitochondrial code and universal code

| | Amino acid to be translated | |
|---|---|---|
| Codon | Universal code | Mitochondrial code |
| TGA | STOP | Trp |
| ATA | Ile | Met |
| CTA or CTT | Leu | Thr |

The nucleotide sequence of ENS2 is known (JP-B-7-77556; Nakagawa, K., Morishima, N., and Shibata, T., J. Biol. Chem. 266, 1977–1984 (1991)). When ENS2 is expressed in a general expression system such as *E.coli* according to the universal code, the translation is interrupted at TGA where it is read as a stop codon as can be appreciated from Table 1 (for example, ENS2 described in JP-B-7-77556 includes a stop codon TGA at nucleotides 97–99). While ATA is read as Ile according to the universal code, it is read as Met according to the mitochondrial code.

In order to construct a normal mass-expression system for ENS2, it is necessary to modify the genetic code of ENS2 such that the amino acid sequence obtained upon expression in a general expression system (e.g., *E.coli*) is identical to an amino acid sequence as expressed in a mitochondrial expression system. Thus, according to the present invention, a codon for Trp (TGA) according to the mitochondrial code (Table 1) is substituted for codon (TGG) that will be translated into Trp according to the universal code. Such substitution is also applied to ATA, and CTA and CTT that are translated into Ile and Leu, respectively, according to the universal code (Table 1). There is no need of substituting other degenerating codons which code for Ile or Leu according to the universal code.

Basically, there are 37 amino acids as the candidates for modification within the amino acid sequence of the smaller subunit of SceI (476 amino acids). Their positions are shown in FIG. 1 and Table 2. As to the endonuclease from *Saccharomyces uvarum* (SuvI), Gly at 217 and Asn at 346 (FIG. 1) are additionally substituted for Lys and Asp, respectively, so that a total of 39 amino acids are modified. It is not necessary to substitute all of the above 37 or 39 amino acids. The number of substitution may be 36, or 35 or less. Translations into codes unique to mitochondria may not be complete as long as the 26 nucleotides (SEQ ID NO:1) mentioned later are recognized by the endonuclease. The positions of substitution are summarized in Table 2 below.

TABLE 2

| Position of substitution | Amino acid to be translated before modification | Amino acid to be translated after modification |
|---|---|---|
| 33, 54, 247, 320, 433 | STOP | Trp |
| 35, 40, 45, 48, 65, 80, 86, 92, 107, 109, 111, 123, 154, 163, 168, 171, 177, 248, 313, 335, 347, 399, 465 | Ile | Met |
| 49, 99, 130, 135, 222, 267, 276, 395, 426 | Leu | Thr |

Substitution of the amino acids is conducted by substituting the nucleotide sequence of the gene encoding the amino acids for another nucleotide sequence (site-directed mutagenesis). Examples of mutagenesis include but not limited to the site-directed mutagenesis method by T. Kunkel (Kunkel, T. A., Proc. Natl. Acad. Sci. U.S.A. 82, 488–492 (1985)) and the Gapped duplex method. There is also a modified version of Kunkel method in which a maximum of 16 oligonucleotides for modification are simultaneously used (instead of using 1 or 2 oligonucleotides as the usual Kunkel method) to efficiently substitute a plurality of sites. According to the present invention, mutation can be introduced by using a mutation introduction kit (for example, Mutant-K (Takara Shuzo, Co., Ltd.) or Mutant-G (Takara Shuzo, Co., Ltd.)) that utilizes site-directed mutagenesis, or by using LA PCR in vitro Mutagenesis series kit (Takara Shuzo, Co., Ltd.).

The oligonucleotides are designed and synthesized using the nucleotide sequence of ENS2 as a template (1431 base pairs: Nakagawa, K. et al., J. Biol. Chem. 266, 1977–1984 (1991); JP-B-7-77556) such that at least one base that is to be introduced with the mutation is flanked by about 8 to 30 bases (each oligonucleotide having a total of about 18 to 60 bases). The oligonucleotides can be obtained through chemical synthesis using a usual synthesizer.

(2) Preparation of endonuclease gene which has been introduced with mutation

Each of the oligonucleotides obtained as described in (1) above is phosphorylated at 5' end, synthesized using ENS2 as a template and subjected to ligation reactions. These reactions can be performed using T4 Polynucleotide Kinase (Takara Shuzo, Co., Ltd.), T4 DNA polymerase (Takara Shuzo, Co., Ltd.), T4 DNA ligase (Takara Shuzo, Co., Ltd.) or the like.

The nucleotide sequence of the thus-obtained DNA is determined. The determination of the nucleotide sequence may be conducted according to a known method such as Maxam-Gilbert chemical modification method or a dideoxynucleotide chain termination method using M13 phage. Generally, the sequence is determined by using an automatic nucleotide sequencer (e.g., ALF (Pharmacia), 373A DNA sequencer (Perkin-Elmer), etc.).

SEQ ID NOS:2 and 3 exemplify the nucleotide sequence of the gene of the present invention and the amino acid sequence of the endonuclease of the present invention, respectively. The endonuclease of the invention acquires the essential function of endonuclease SceI or SuvI, i.e., the function of recognizing the consensus sequence "CANRYN-NANNCYYGTTW" and a sequence similar thereto, by linking to the larger subunit of natural endonuclease. The endonuclease of the invention exerts the function of the smaller subunit of the natural endonuclease and can specifically recognize the 26 bases represented by "GCCCAGA-CATATCCCTGAATGATACC" (SEQ ID NO:1).

The endonuclease of the present invention may include at least one mutation such as deletion, substitution, addition or the like of the amino acid as long as it can specifically recognize the above 26 bases (SEQ ID NO:1).

For example, the amino acid sequence represented by SEQ ID NO:3 may include deletion of at least one, preferably 1 to 10, more preferably 1 to 5 amino acids; addition of at least 1, preferably 1 to 10, more preferably 1 to 5 amino acids; or substitution of at least 1, preferably 1 to 10, more preferably 1 to 5 amino acids for another amino acids. The endonuclease of the invention does not have to include mutations of all of the above-described 37 or 39 amino acids as long as it can recognize the above 26 bases (SEQ ID NO:1).

The phrase "can recognize" as used herein refers to the function of the endonuclease of the invention to bind to a site of the 26 bases within the gene and to cleave the gene such that the 26 base pairs are separated into two fragments with staggered ends.

DNA that can hybridize with the above gene (SEQ ID NO:2) under stringent conditions may also be included in the gene of the present invention. The stringent conditions are, for example, a sodium concentration of 15 to 900 mM and a temperature of 37 to 70° C., preferably 68° C.

(3) Preparation and transformation of recombinant vector (i) Preparation of recombinant vector A recombinant vector of the invention may be obtained by ligating (inserting) the gene of the invention to (into) a suitable vector. The vector for inserting the gene of the invention is not limited to a specific one as long as it is replicable in a host cell. Examples of such vector include but not limited to plasmid DNA and phage DNA.

The plasmid DNA is, for example, plasmid from *E.coli* (e.g., pRSET, pTZ19R, pBR322, pBR325, pUC118, pUC119, etc.), plasmid from bacillus (e.g., pUB110, pTP5, etc.), or plasmid from yeast (e.g., YEp13, YEp24, YCp50, etc.). The phage DNA is, for example, λ phage or the like. Similarly, an animal virus vector such as a retrovirus or vaccinia virus vector, or an insect virus vector such as a baculovirus vector may also be used.

In order to insert the gene of the invention into the vector, the purified DNA is cleaved with a suitable restriction enzyme. Then, the cleaved fragment is inserted into the restriction site or a multicloning site of the suitable vector DNA.

The gene of the present invention should be integrated into the vector such that the gene is able to function. If desired, the vector of the invention may include, other than the gene of the invention and the promoter, for example, a cis-element (e.g., an enhancer), a splicing signal, a poly(A) tail signal, a selective marker, and a ribosome binding sequence (SD sequence). Examples of the selective marker include dihydrofolate reductase gene, ampicillin-resistant gene and neomycin-resistant gene.

(ii) Preparation of transformant

A transformant of the invention may be obtained by introducing the recombinant vector of the invention into a host cell in such a manner that the gene of interest is capable to be expressed. The host cell is not limited to a specific one as long as it can express the DNA of the present invention. Bacteria such as genus Escherichia (e.g., *Escherichia coli*), genus Bacillus (e.g., *Bacillus subtilis*), genus Pseudomonal (e.g,. *Pseudomonas putida*), genus Rhizobium (e.g., *Rhizobium meliloti*), yeast such as *Schizosaccharomyces pombe*, animal cells (e.g., COS and CHO cells), and insect cells (e.g., Sf9 and Sf21) are exemplified.

When a bacterium such as *E.coli* is used as the host, it is preferable that the recombinant vector of the present invention is capable of autonomous replication and includes a promoter, a ribosome binding sequence, the gene of the invention and a transcription termination sequence. The recombinant vector may also include a gene for controlling the promoter.

As the *E.coli*, *E. coli* K12 and DH1 are exemplified and as bacillus, *Bacillus subtilis* MI 114 and 207–21 are exemplified.

As the promoter, any promoter may be used as long as it can be expressed in the host cell like *E.coli*. For example, a promoter derived from *E.coli* or a phage, e.g., trp promoter, lac promoter, $p_L$ promoter or $p_R$ promoter, may be used. Artificially designed and modified promoter like tac promoter may also be used.

The recombinant vector may be introduced into the bacterium according to any method for introducing DNA into a bacterium. For example, calcium ion method (Cohen, S. N. et al., Proc. Natl. Acad. Sci., USA, 69: 2110–2114 (1972)) and an electroporation method may be employed.

An yeast such as *Saccharomyces cerevisiae, Saccharomyces uvarum, Schizosaccharomyces pombe* or *Pichia pastoris* may also be used as the host. In this case, the promoter may be any promoter that can be expressed in the yeast. Examples of such promoter include but not limited to gal1 promoter, gal10 promoter, heat shock protein promoter, MF 1 promoter, PHO5 promoter, PGK promoter, GAP promoter, ADH promoter and AOX1 promoter.

The recombinant vector may be introduced into the yeast by any method for introducing DNA into an yeast. For example, electroporation method (Becker, D. M. et al., Methods Enzymol., 194, 182–187 (1990)), spheroplast method (Hinnen, A. et al., Proc. Natl. Acad. Sci., USA, 75, 1929–1933 (1978)), or lithium acetate method (Itoh, H., J. Bacteriol., 153, 163–168 (1983)) may be employed.

An animal cell such as simian cell COS-7, Vero, Chinese hamster ovary cell (CHO cell), mouse L cell, rat GH3 or human FL cell may also be used as the host. As a promoter, for example, SR promoter, SV40 promoter, LTR promoter or CMV promoter may be used. Other than these promoters, an early gene promoter of human cytomegalovirus may also be used.

The recombinant vector may be introduced into the animal cell, for example, by an electroporation method, a calcium phosphate method or a lipofection method.

An insect cell such as Sf9 cell, Sf21 cell or the like may also be used as the host. The recombinant vector may be introduced into the insect cell, for example, by a calcium phosphate method, a lipofection method or an electroporation method.

(5) Production of endonuclease

The endonuclease of the present invention may be obtained by culturing the above-described transformant, and recovering the endonuclease from the culture thereof. The term "culture" as used herein refers to a culture supernatant, a cultured cell or microbial cell, or a cell or microbial cell debris.

The transformant of the invention is cultured according to a general method used for culturing the host.

A medium for culturing the transformant obtained from a microorganism host such as *E.coli* or yeast may be either a natural or a synthetic medium as long as it contains carbon sources, nitrogen sources, inorganic salts and the like assimilable by the microorganism, and as long as it can efficiently culture the transformant.

As carbon sources, carbohydrate such as glucose, fructose, sucrose, starch; organic acids such as acetic acid, propionic acid; and alcohols such as ethanol and propanol may be used.

As nitrogen sources, ammonia; ammonium salts of inorganic or organic acids such as ammonium chloride, ammonium sulfate, ammonium acetate, ammonium phosphate; other nitrogen-containing compounds; Peptone; meat extract; corn steep liquor and the like may be used.

As inorganic substances, potassium dihydrogen phosphate, dipotassium hydrogen phosphate, magnesium phosphate, magnesium sulfate, sodium chloride, iron(II) sulfate, manganese sulfate, copper sulfate, calcium carbonate and the like may be used.

The cultivation is generally performed under aerobic conditions such as shaking or aeration agitating conditions at 37° C. for 12 to 18 hours. During the cultivation, pH is maintained at 6.5 to 7.5, preferably 7.0. pH is regulated with an inorganic or organic acid, an alkali solution or the like.

During the cultivation, an antibiotic such as ampicillin, tetracycline or the like may be added to the medium if necessary.

When culturing a microorganism transformed with an expression vector using an inducible promoter, an inducer may be added to the medium at need. For example, when a microorganism transformed with an expression vector using Lac promoter or trp promoter is cultured, isopropyl 1-thio-β-D-galactoside (IPTG) or indoleacetic acid (IAA) may be added to the medium, respectively.

A transformant obtained by using an animal cell host may be cultured in a generally used medium such as RPMI1640 medium or DMEM medium, or a medium obtained by supplementing the generally used medium with fetal bovine serum and the like.

The cultivation is generally conducted under 5% $CO_2$ at 37° C. for 1 to 3 days. During the cultivation, an antibiotic such as kanamycin, penicillin or the like may be added to the medium.

After the cultivation, where a microbial cell or a cell intracelluraly produced endonuclease of the invention, the endonuclease is extracted by disrupting the microbial cell or the cell. Where a microbial cell or a cell extracellularly produced endonuclease of the invention, the culture solution is directly used. Alternatively, the microbial cell or the cell is removed through centrifugation or the like before isolating and purifying the endonuclease of the invention from the culture through a general biochemical method for protein isolation and purification such as ammonium sulfate precipitation, gel chromatography, ion exchange chromatography, affinity chromatography, or a combination thereof.

EXAMPLES

Hereinafter, the present invention will be described in detail by way of examples which do not limit the technical scope of the present invention.

Example 1

Figure 3:
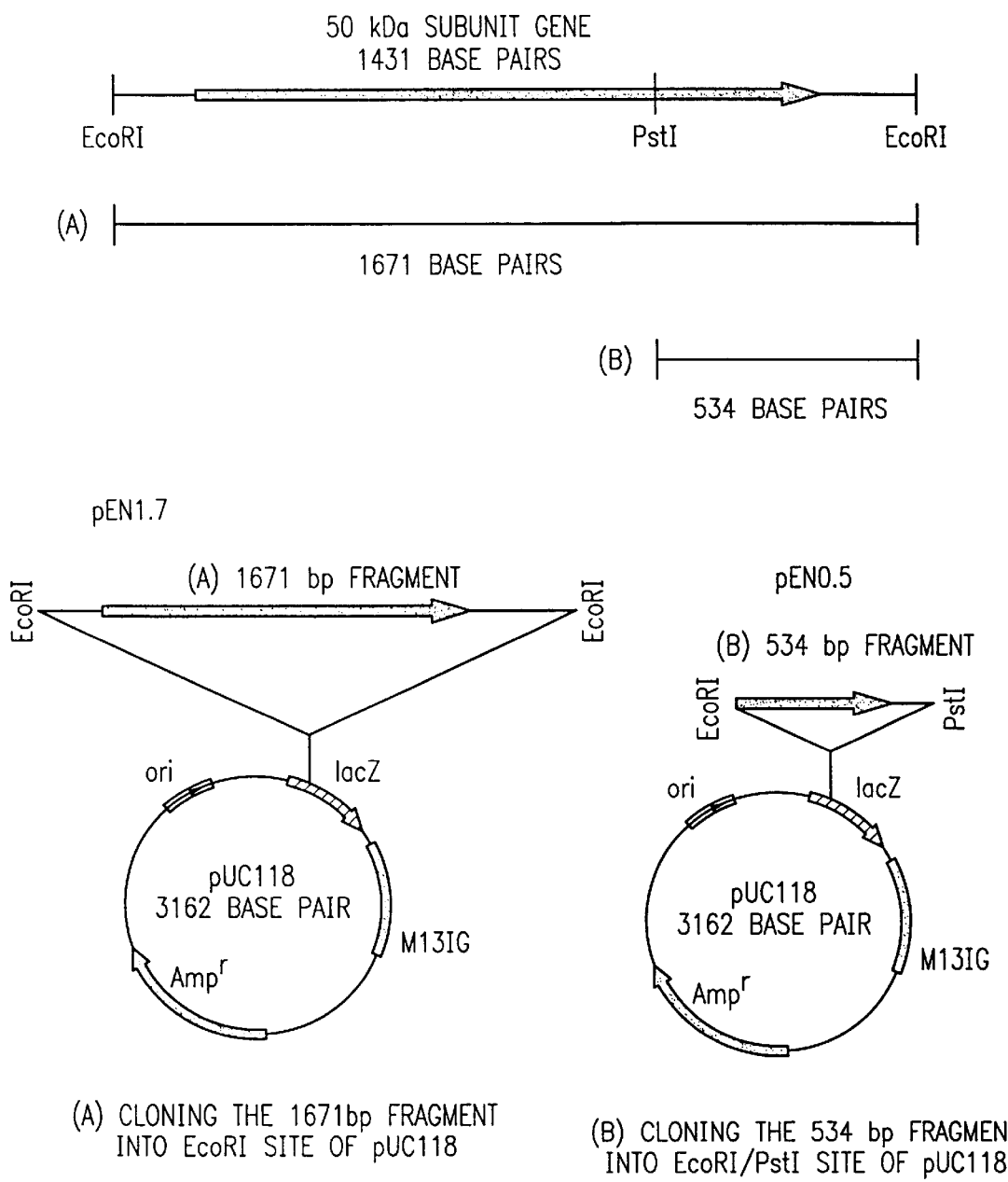
FIG. 3 shows the steps for constructing plasmids pEN1.7 and pEN0.5.

Preparation of Single-stranded Template DNA Encoding Subunit of SceI and Containing Deoxyuracil Endo.SceI 50 kDa subunit gene ENS2 (1431 base pairs; Nakagawa, K., Morishima, N., and Shibata, T., *J. Biol. Chem.* 266, 1977–1984 (1991)) was modified simultaneously within two regions of the gene, i.e., within the upstream moiety of 1.0 kilobase pair and the downstream moiety of 0.4 kilobase pair. For this purpose, EcoRI/EcoRI fragment (1671 base pairs) containing the full-length 50 kDa subunit gene (Nakagawa, K., Morishima, N., and Shibata, T. *J., Biol. Chem.* 266, 1977–1984 (1991)), and PstI/EcoRI fragment (534 base pairs) containing the downstream moiety of the 50 kDa subunit gene were separately cloned into phagemids pUC118 (Takara Shuzo, Co., Ltd.), and were named plasmids pEN1.7 and pEN0.5, respectively (FIG. 3). These phagemids were introduced into *E.coli* strains CJ236 (Takara Shuzo, Co., Ltd.) for transformation. The transformant *E.coli* strains were shake cultured at 37° C. for 12 hours or longer so as to prepare pre-culture solutions. Twenty µl of each pre-culture solution was added to 2 ml of 2×YT culture medium containing ampicillin (100 µg/ml) (Sambrook, J., Fritsch, E. F., and Maniatis, T., *Molecular Cloning: a laboratory Manual*, Second Edition, Cold Spring Harbor Laboratory Press, Cold Spring Harbor, N.Y. (1989)) and cultured at 37° C. for 1 hour. To each medium, helper phage M13KO7 ($2.0 \times 10^{12}$ plaque-forming unit (pfu); Takara Shuzo, Co., Ltd.) was added to constitute 0.4% in volume of the medium, and the resultant was cultured at 37° C. for 1 hour. Thereafter, kanamycin (100 µg/ml) was added and the resultant was cultured at 37° C. for 14 hours. Phage particles released from *E.coli* into the media during the cultivation were recovered. Specifically, 1.5 ml of each culture solution was centrifuged (14,000 rpm, 5 min.) in a micro-centrifuge. 1.2 ml of the supernatant was collected and centrifuged under the same conditions to completely remove the cell, thereby obtaining 1.0 ml of the supernatant. Subsequent procedure for preparing the DNA was conducted according to DNA purification of bacteriophage M13 phage summarized in the experimental text of J. Sambrook et al. (Sambrook, J., Fritsch, E. F., and Maniatis, T. *Molecular Cloning: a laboratory Manual,* Second Edition, Cold Spring Harbor Laboratory Press, Cold Spring Harbor, N.Y. (1989)).

Example 2

Synthesis of Oligonucleotides for Introducing Site-directed Mutation (i) Synthesis of single strand 50 kDa subunit gene ENS2 is encoded by mitochondria genome, and thus includes genetic code unique to mitochondria (Table 1). In order to subject ENS2 to a general mass-expression system, these unique codons must be replaced so as to correspond to the universal code. According to Example 2, the bases were substituted by using a modified method of T. Kunkel (Kunkel, T. A., *Proc. Natl. Acad. Sci. U.S.A.* 82, 488–492 (1985)). Whereas the general Kunkel method uses only one or two oligonucleotides for modification, the present method simultaneously used a maximum of 16 oligonucleotides for efficient substitution at multiple sites.

33 oligonucleotides were designed which each contained the base to be substituted flanked by approximately 10 to 15 bases (Table 3).

TABLE 3

| | |
|---|---|
| 1. AAAAGACTG<u>G</u>ATTATAGAA<br>(A) | (SEQ ID NO:6) |
| 2. TGAATATAT<u>G</u>TATAAATTT<br>(A) | (SEQ ID NO:7) |
| 3. TATTAAATG<u>G</u>GATAATAAT<br>(A) | (SEQ ID NO:8) |
| 4. TATTAGATAT<u>G</u>TATTATAATG<br>(A) | (SEQ ID NO:9) |
| 5. TACACCTAT<u>G</u>TCTAATAAA<br>(A) | (SEQ ID NO:10) |
| 6. AAAATATTAT<u>G</u>GATTATAAA<br>(A) | (SEQ ID NO:11) |
| 7. TTTTATATTTTAAATAAAAT<u>G</u>AAAT<u>G</u>GAAAT<u>G</u>GATAATTATAATAATAATA<br>(A)<br>(A)<br>(A)<br>(SEQ<br>ID<br>NO:12) | |
| 8. AAAATATTAT<u>G</u>AATAATTTAA<br>(A) | (SEQ ID NO:13) |
| 9. ACTATCTAATATTGAA<u>AC</u>TAATTTATCTAATAATTT<br>(CT) | (SEQ ID NO:14) |
| 10. TTATTTAAT<u>G</u>GATAAATAT<br>(A) | (SEQ ID NO:15) |
| 11. ATAAATATAT<u>G</u>AAATATTTAG<br>(A) | (SEQ ID NO:16) |
| 12. ATAATTATAT<u>G</u>TTTAATAATA<br>(A) | (SEQ ID NO:17) |
| 13. GGAGGTATTACAATT<u>AC</u>TAATCATGCTAATGAT<br>(CTA) | (SEQ ID NO:18) |
| 14. TTTTAGTAGAAAAAT<u>G</u>GATGGATACTTTAAAAGATA<br>(A)<br>(A) | (SEQ ID NO:19) |
| 15. AGCTAAAGAAAAGATTTTT<u>AC</u>TAATATTTATAATAATTA<br>(CT) | (SEQ ID NO:20) |
| 16. AAATATTAT<u>G</u>GATATTAAA<br>(C) | (SEQ ID NO:21) |
| 17. TAATTATTG<u>G</u>TTATCTGG<br>(A) | (SEQ ID NO:22) |
| 18. ATCATCTAT<u>G</u>TATAATCCT<br>(A) | (SEQ ID NO:23) |
| 19. TTAAAAATAT<u>G</u>AGACCTAG<br>(A) | (SEQ ID NO:24) |
| 20. GATGAATTAAT<u>G</u>AAATTTATTTA<br>(A) | (SEQ ID NO:25) |
| 21. ATTAAATTTAGATTTAAT<u>AC</u>TTTTATTAAATCATATAAT<br>(CTA) | (SEQ ID NO:26) |
| 22. TATAATAAATATATTAATAT<u>G</u>CATAATGCACGTAAACC<br>(A) | (SEQ ID NO:27) |
| 23. TAAATTTTTAATAAATAATAT<u>G</u><u>AC</u>TTGTTTTATTAAAT<u>G</u>gGA<br>(ACTA) | (SEQ ID NO:28) |
| 24. AAGATTAAT<u>G</u>AATTCAAAA<br>(A) | (SEQ ID NO:29) |
| 25. GATTATAAATTATTATAT<u>AC</u>TTATTTTTATATTTTAAAT<br>(CT) | (SEQ ID NO:30) |
| 26. gAATAATTTAAATTATAAA<u>AC</u>TTCTAATATTGAAacTA<br>(CTA) | (SEQ ID NO:31) |
| 27. TTCTCTATTAATATTAAA<u>AC</u>TAATTTAGCTAAAGAAA<br>(CT) | (SEQ ID NO:32) |
| 28. AAATTATTTACCAGAACT<u>AC</u>TGATGAATTAATgAAATT<br>(CT) | (SEQ ID NO:33) |
| 29. CATATAATT<u>G</u>GAATAATAGA<br>(A) | (SEQ ID NO:34) |
| 30. AATTTTTAAT<u>G</u>AATAATATg<br>(A) | (SEQ ID NO:35) |
| 31. TTTAGATAT<u>G</u>TTAAATATg<br>(A) | (SEQ ID NO:36) |
| 32. ATATgTTAAATAT<u>G</u>ATTCCTAATAA<br>(A) | (SEQ ID NO:37) |
| 33. CTGgATTAT<u>G</u>GAATATGAAT<br>(A) | (SEQ ID NO:38) |

In Table 3, the base(s) in parentheses underneath each sequence represent the original base(s) that was (were) substituted for the underlined base(s). The bases shown in small letters represent those which have already replaced the original oligonucleotide.

The lengths of the oligonucleotides vary within the range of 18 to 52 bases and they include mutation of 1 to a maximum of 4 residues. These oligonucleotides were used for substituting 50 base pairs of the 1431 bp 50 kDa subunit gene to modify 37 codons. 5' end of each oligonucleotide was phosphorylated so as to allow the DNA ligase reaction described later. The composition of the reaction mixture for the phosphorylation is shown below:

100 mM Tris-HCl (pH 8.0)
10 mM magnesium chloride
7 mM dithiothreitol
1 mM ATP, 1 μM oligonucleotide
T4 polynucleotide kinase (15 units)
Total amount 30 μl The reaction mixture was subjected to phosphorylation reaction at 37° C. for 15 min., and then the enzyme was inactivated through a treatment at 70° C. for 10 min.

(ii) Synthesis of complementary strand

The oligonucleotides obtained in (i) were treated as follows to obtain double-strands. Compositions of the annealing buffer and the elongation reaction buffer are shown below:

Annealing Buffer 200 mM Tris-HCl (pH 8.0)
100 mM magnesium chloride
500 mM sodium chloride
10 mM dithiothreitol Elongation Reaction Buffer 50 mM Tris-HCl (pH 8.0)
5 mM dithiothreitol
60 mM ammonium acetate
0.5 mM each of dNTPs (A, C, T, G)
5 mM magnesium chloride
1 mM nicotinamido adenine dinucleotide Distilled water was added to 1 μl of the annealing buffer and 0.2 pmol of the single-stranded template DNA, resulting in a total amount of 10 μl. One μl of the solution was dispensed to be mixed with 1 μl of the phosphorylated oligonucleotide solution. The resultant mixture was left to stand at 65° C. for 15 min. and then at 37° C. for 15 min., whereby the oligonucleotide annealed to the single-stranded DNA. To the solution, 25 μl of the elongation buffer, 60 units of *E.coli* DNA ligase and 1 unit of T4 DNA polymerase were added and left to stand at 25° C. for 2 hours so as to synthesize a complementary strand. Three μl of 0.2 M ethylene diamine tetra acetic acid tetrasodium salt (pH 8.0) was added to terminate the enzyme reaction, after which the enzyme was inactivated through treatment at 65° C. for 5 min. This reaction solution was directly used for the subsequent transformation.

Example 3

Transformation

*E.coli* BMH71-18 muts (Takara Shuzo, Co., Ltd.) was used such that the nucleotide sequence of the wild-type DNA strand (the single-stranded DNA prepared with CJ236) in the double-stranded plasmid DNA obtained through the complementary strand synthesis was substituted for a mutant type. In this *E.coli* strain, deoxyuracil contained in the single-stranded DNA prepared with CJ236 was hydrolyzed by enzyme uracil-DNA glycosylase and then synthesized again using the DNA strand containing the substituted base as a template (Lindahl, T., *Ann. Rev. Biochem.* 51, 61–87 (1982).

The whole reaction mixture with the synthesized complementary strand was added to 100 μl solution containing competent cell of BMH71-18 muts. *E.coli* competent cell was prepared according to the method of H. Inoue et al. (Inoue, H., Nojima, H., and Okayama, H., *Gene* 96, 23–28 (1990)).

To the solution, a medium was added and left at 37° C. for 1 hour. Then, 30 μl of helper phage (supra) was added and left to stand at 37° C. for another 30 min. for infection to take place. 40 μl of culture solution of BMH71-18 intracellularly containing both the helper phage and the plasmid was fractionated and added to 2 ml of 2×YT medium containing ampicillin (100 μg/ml) and kanamycin (100 μg/ml). The resultant medium was shake cultured at 37° C. for 16 to 20 hours to produce a phage.

The microbial cell was removed through centrifugation (14,000 rpm, 5 min.). The supernatant was collected which contained the phage particle incorporating the single-stranded DNA of the plasmid with the substituted base. With 20 μl of the supernatant, 80 μl of strain MV1184 (Takara Shuzo, Co., Ltd.) which has been cultured for 12 hours or longer was mixed and left to stand at 37° C. for 10 min. so as to inject the single-stranded DNA of the phage into the cell. The strain MV1184 containing the plasmid resulting from replication of the integrated single-stranded DNA was inoculated to an LB agar medium containing 100 μg/ml ampicillin (Sambrook, J., Fritsch, E. F., and Maniatis, T., *Molecular Cloning: a laboratory Manual*, Second Edition, Cold Spring Harbor Laboratory Press, Cold Spring Harbor N.Y. (1989)) for selection. The nucleotide sequences of the 50 kDa subunit genes were analyzed for some clones with an automatic sequencer ALF (Pharmacia) to confirm the incorporation of the predetermined substitutions. The fluorescent primer for the analysis of the nucleotide sequence was purchased from Pharmacia (Uppsala, Sweden). The DNA sequencing reaction was based on the Sanger method (Sanger, F. et al., *Proc. Natl. Acad. Sci.*, 74, 5463–5467 (1977)) according to the protocol of Pharmacia.

For the starting material, plasmid pEN1.7, forty nucleotide substitutions were performed by 9 cycles of the mutagenic process, while 10 nucleotide substitutions were performed for pEN0.5 by 4 cycles of such process. Once all of the substitutions were confirmed, the upstream and downstream moieties were linked at the PstI cleavage site, thereby obtaining a gene of the invention encoding the 50 kDa subunit with complete substitutions (FIG. 4, SEQ ID NO:2).

Example 4

Construction of Expression Plasmid for 50 kDa Subunit

For facilitating the linking between the modified 50 kDa subunit gene and the vector for inducing expression thereof, restriction sites were introduced into the 5' and 3' terminuses of the modified gene through polymerase chain reaction (PCR). The reaction was performed using Taq DNA polymerase (Takara Shuzo, Co., Ltd.) according to the protocol of the manufacturer. Sequences of the used primers are shown below.

5'-CCGGATCCATGAAAAAAC-3' (SEQ ID NO:4)
5'-GGGTCGACTTATTTAATGTATCC-3' (SEQ ID NO:5)

The underlined parts are the newly introduced BamHI and SalI recognition sequences. The reaction was performed through 25 cycles of: 94° C. for 1 min.; 45° C. for 2 min.; and 72° C. for 3 min.

The DNA fragment (1447 base pairs) amplified by PCR was separated through agarose (0.8%) gel electrophoresis (Sambrook, J., Fritsch, E. F., and Maniatis, T. *Molecular Cloning: a laboratory Manual,* Second Edition, Cold Spring Harbor Laboratory Press, Cold Spring Harbor, N.Y. (1989)) and stained with ethidium bromide for confirmation. The fragment was recovered from the agarose gel using Geneclean kit (BIO101, California, USA).

The recovered DNA fragment was treated with BaMHI and SalI, and subcloned into pRSET (Invitrogen Corp.) and pTZ19R (Pharmacia) to obtain pSC50 and pTZSC50, respectively. Plasmid pSC50 was used for inducing the expression. Plasmid pTZSC50 was subjected to DNA sequencing using fluorescent primer (supra) so as to confirm that no extra mutation had been introduced during the PCR.

Example 5
Induction of Expression of 50 kDa Subunit

Expression plasmid pSC50 was introduced into a competent cell of *E.coli* BL21 (DE3) pLysS (Invitrogen Corp.). The transformant cell was pre-cultured through shake cultivation in an LB liquid medium containing ampicillin (150 μg/ml) and chloramphenicol (34 μg/ml) (Sambrook, J., Fritsch, E. F., and Maniatis, T. *Molecular Cloning: a laboratory Manual,* Second Edition, Cold Spring Harbor Laboratory Press, Cold Spring Harbor, N.Y. (1989)) at 37° C. overnight. The pre-cultured solution (4% in volume of a resultant culture) was centrifuged (2,500×g, 10 min.) to recover the microbial cell. This precipitate was suspended in a small amount of fresh medium, which was then added to a liquid medium. Shake cultivation (37° C.) was performed until the suspension level at 600 nanometers (nm) (OD600) of about 0.5 was obtained. Thereafter, shake cultivation was continued at 18° C. When the OD600 became about 0.8, isopropyl 1-thio-β-D-galactoside (IPTG) was added to the final concentration of 0.4 mM to initiate induction of expression of the 50 kDa subunit. After performing shake cultivation at 18° C. for another 12 hours, *E.coli* was recovered through centrifugation, rapidly frozen with liquid nitrogen and stored at −80° C.

Example 6
Purification of 50 kDa Subunit from *E.coli*

The microbial cell stored at −80° C. was melted at room temperature. The subsequent treatments were conducted at 4° C. or on ice. The microbial cell was suspended in Buffer A (20 mM Tris-HCl buffer (pH 8.0), 500 mM sodium chloride, 5 mM imidazole, 1 mM phenylmethylsulfonyl fluoride (PMSF; Sigma Aldrich Japan K.K., Tokyo, Japan), 0.1% NP-40 (Nacalai Tesque, Inc., Kyoto, Japan)). The resultant suspension was rapidly frozen with liquid nitrogen and melted under running water to disrupt the *E.coli*. The suspension was treated for 5 times with an ultrasonicator (UR-200P, Tomy Seiko Co., Ltd., Tokyo, Japan) at a maximum output for 30 sec.

The treated solution was centrifuged (39,000×g, 20 min.) at 4° C. The obtained supernatant was filtrated through 0.45 μm Mylex filter (Millipore, Mass., USA). The sample was placed in a column (φ10 mm, 2.0 ml) loaded with Probond Nickel Chelate Resin (Invitrogen Corp.) which had been equibralized with Buffer A. Then, the sample was washed with 20 ml of Buffer A (ten times the volume of the resin). After another washing with 12 ml Buffer A containing 60 mM imidazole (six times the volume of the resin), the resultant was subjected to gradient elution with 60–50 mM imidazole-containing Buffer A (total amount of 80 ml). The eluted fraction was subjected to sodium dodecyl sulfate-polyacrylamide gel electrophoresis (Laemmli, U. K. *Nature,* 227, 680–685 (1970)) and stained with Coomasie brilliant blue to confirm the presence of the 50 kDa subunit. The fraction containing the 50 kDa subunit was dialyzed against Buffer B (20 mM Tris-HCl buffer (pH 7.5), 300 mM sodium chloride, 1 mM ethylenediaminetetraacetic acid tetrasodium salt, 1 mM dithiothreitol). The purified protein was quantified using Protein assay agent (Bio-Rad, California, USA) according to the micro-assay method of the manufacturer. Bovine serum albumin solution (Sigma Aldrich Japan K.K.) was used as a standard protein. As a result, 300 μg of purified protein was obtained from 25 g (wet weight) of the microbial cell.

Example 7
Measurement of Endonuclease Activity

A substrate for measuring an endonuclease activity of the 50 kDa subunit was prepared as follows. An EcoRI/EcoRI fragment containing oli2 region on mitochondria DNA within which Endo.SceI is known to be cleaved (1671 base pairs; Nakagawa, K. et al., *EMBO J.* 11, 2707–2715 (1992)) was subcloned into phagemid pUC119 (Takara Shuzo, Co., Ltd.), the resultant called pY673L (FIG. 2). Plasmid pBR322 (Takara Shuzo, Co., Ltd.) was used as a control DNA substrate. Plasmids pY673L and pBR322 were used to transform *E.coli*. Then, the plasmids were extracted from *E.coli* and highly purified using Qiagen column (Qiagen Japan, Tokyo, Japan).

The composition of the reaction solution used for measuring the endonuclease activity of the 50 kDa subunit is shown below:

50 mM Tris-HCl buffer (pH 8.0)

50 mM sodium chloride 10 mM magnesium chloride 1 mM dithiothreitol 25 ng substrate DNA (pY673L or pBR322 which has been linearized with restriction enzyme ScaI (FIG. 2))

0.4 to 60 ng 50 kDa subunit

Total volume 30 μl

After performing the DNA cleavage reaction at 37° C. for 30 min., ethylenediaminetetraacetic acid tetrasodium salt and sodium dodecyl sulfate were added to final concentrations of 10 mM and 0.3%, respectively, to terminate the reaction. The cleaved DNA was subjected to 0.8% agarose electrophoresis either directly or after concentrating the DNA through phenol extraction and ethanol precipitation.

After the electrophoresis, the gel was stained with ethidium bromide (Sigma Aldrich Japan K.K.) or SYBR Green (Takara Shuzo, Co., Ltd.) to confirm cleavage of DNA. The DNA was detected using FMBIO Imaging device (Takara Shuzo, Co., Ltd.) to determine the DNA cleavage.

Example 8
Detection of Sequence-specific Endonuclease

The dimeric Endo.SceI recognizes and cleaves in vivo and in vitro 26 base pairs similar to the consensus sequence within the oli2 gene region on the mitochondria DNA (Nakagawa, K., Morishima, N., and Shibata, T., *EMBO J.* 11, 2707–2715 (1992)) (FIG. 2). The purified 50 kDa subunit of Endo.SceI cleaved a specific sequence (SEQ ID NO:1) by itself.

Figure 5A:
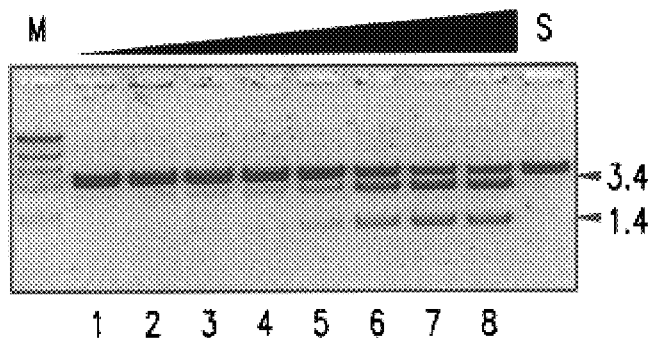
FIGS. 5A and 5B are photographs of electrophoresis showing sequence-specific endonuclease activities of the 50 kDa subunit of the modified SceI.

Specific cleavage of oli2 with the 50 kDa subunit using plasmid pY673L containing oli2 as the substrate was confirmed (FIG. 5A). Referring to FIG. 5A, Lanes 1 to 8 are the results obtained with 0.5, 1.0, 2.0, 4.0, 8.0, 16.0, 32.0 and 64.0 ng of the 50 kDa subunits, respectively. With 64 ng of 50 kDa subunit, 60% of pY673L (25 ng) in the reaction solution was sequence-specifically cleaved at 37° C. within 30 min., whereby DNA fragments of 3.4 and 1.4 kilobases were detected.

Figure 5B:
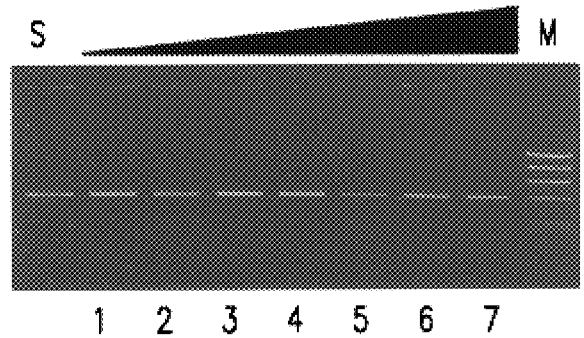

DNA was not cleaved with the 50 kDa subunit using plasmid pBR322 as the substrate and no cleavage fragment was detected (FIG. 5B). Referring to FIG. 5B, Lanes 1 to 7 are the results obtained with 2.3, 4.5, 9.0, 18.0, 36.0, 72.0 and 144 ng of the 50 kDa subunits, respectively. When an excessive amount (200 ng) of the 50 kDa subunit was used, no cleavage was found with pBR322 or other DNAs (mitochondria DNA (80 kilobase pairs) from bud yeast strain, E.coli phage λ DNA (47 kilobase pairs), and bacillus phage φ105 DNA (38 kilobase pairs) which did not contain specific sequence (26 base pairs) within oli2 gene region).

Example 9

Mass Production of 50 kDa Subunit from Saccharomyces Uvarum and Detection of the Activity Thereof Endo.SuvI 50 kDa subunit, a homologous protein of Endo.SceI 50 kDa subunit from *Saccharomyces cerevisiae* is present in *Saccharomyces uvarum* (Nakagawa, K., Morishima, N., and Shibata, T., J. Bio. Chem. 266, 1977–1984 (1991)). Both subunits have 476 amino acid residues but there are two differences in amino acid level between them. The amino acid differences between Endo.SceI and Endo.SuvI 50 kDa subunits are shown in FIG. 6A.

A mass-expression gene for Endo.SuvI 50 kDa subunit was prepared by introducing two additional modifications into the modified gene for Endo.SceI 50 kDa subunit. The oligonucleotides used for the substitutions of the amino acids for Endo.SuvI 50 kDa subunit are shown in FIG. 6B. With reference to FIG. 6B, the bases in parentheses correspond to the nucleotide sequence of Endo.SceI 50 kDa subunit. For this purpose, two oligonucleotides were newly synthesized to introduce mutations according to the gene modification method described above. The mutation was confirmed through DNA sequencing. The modified gene was subcloned into pRSET vector (Invitrogen Corp.), which was then introduced into E.coli BL21 (DE3) pLys by transformation method.

Endo.SuvI 50 kDa subunit was expressed and purified according to the method applied to Endo.SceI 50 kDa subunit described above. The purified Endo.SuvI 50 kDa subunit was used to specifically cleave plasmid pY673L.

As a result, Endo.SuvI 50 kDa subunit was equally effective in sequence-specifically cleaving the Endo.SceI 50 kDa subunit cleavage site on plasmid pY673L (FIG. 7A).

Meanwhile, Endo.SuvI 50 kDa subunit did not cleave plasmid pBR322 at all (FIG. 7B). Also, other DNAs (bud yeast mitochondria DNA, bacillus phage φ105 λ DNA and E.coli phage λ DNA which did not contain oli2 gene region) were not cleaved by Endo.SuvI 50 kDa subunit.

In FIGS. 7A and 7B, Lanes 1 to 7 are the results obtained with 2.3, 4.5, 9.0, 18.0, 36.0, 72.0 and 144 ng of 50 kDa subunits, respectively.

According to the present invention, a site-specific endonuclease capable of recognizing a specific nucleotide sequence, a gene encoding the endonuclease, a recombinant vector containing the gene, a transformant containing the vector, and a process for producing the endonuclease are provided. Since the endonuclease of the present invention is capable of recognizing a specific sequence of 26 bases, it is useful in the field of genetic engineering and biochemistry in modifying and mapping DNA for a wide application, i.e., plasmid to genome.

All publications, patents, and patent applications cited herein are incorporated herein by reference in their entirety.

The following are information on sequences described herein:

What is claimed is:

1. A method of cleaving a DNA having a 26 base sequence GCCCAGACATATCCCTGAATGATACC (SEQ ID NO:1), comprising (a) reacting the DNA with a protein comprising the amino acid sequence of SEQ ID NO:3; and
   (b) cleaving the DNA such that said DNA is cleaved within said 26 base region producing staggered ends.

2. A method of detecting DNA having a 26 base sequence GCCCAGACATATCCCTGAATGATACC (SEQ ID NO:1), comprising (a) reacting the DNA with a protein comprising the amino acid sequence of SEQ ID NO:3;
   (b) cleaving the DNA such that said DNA is cleaved within said 26 base region producing staggered ends; and
   (c) detecting the cleaved DNA.

* * * * *